(12) United States Patent
Jääskeläinen et al.

(10) Patent No.: US 10,203,279 B1
(45) Date of Patent: Feb. 12, 2019

(54) OPTICAL MEASURING DEVICE, A REFRACTOMETER AND AN ARRANGEMENT FOR AN OPTICAL MEASUREMENT

(71) Applicant: JANESKO OY, Vantaa (FI)

(72) Inventors: Juha Jääskeläinen, Vantaa (FI); Harri Salo, Vantaa (FI); Ville Lyyra, Helsinki (FI); Tuomo Lautamäki, Klaukkala (FI)

(73) Assignee: JANESKO OY, Vantaa (FI)

( * ) Notice: Subject to any disclaimer, the term of this patent is extended or adjusted under 35 U.S.C. 154(b) by 0 days.

(21) Appl. No.: 15/834,893

(22) Filed: Dec. 7, 2017

(51) Int. Cl.
| | |
|---|---|
| G01N 21/00 | (2006.01) |
| G01N 21/41 | (2006.01) |
| G01N 21/15 | (2006.01) |
| G01N 21/43 | (2006.01) |
| G01M 11/02 | (2006.01) |
| G01J 3/02 | (2006.01) |

(52) U.S. Cl.
CPC ........ G01N 21/4133 (2013.01); G01J 3/0205 (2013.01); G01M 11/0228 (2013.01); G01N 21/15 (2013.01); G01N 21/43 (2013.01); *G01N 2201/0833* (2013.01)

(58) Field of Classification Search
CPC .... G01N 21/4133; G01N 21/15; G01N 21/43; G01N 2201/0833; G01J 3/0205
USPC .......................................................... 73/768
See application file for complete search history.

(56) References Cited

U.S. PATENT DOCUMENTS

| | | | | |
|---|---|---|---|---|
| 6,358,181 | B1* | 3/2002 | Friedmann | F16H 61/662 477/37 |
| 2002/0018200 | A1* | 2/2002 | Salo | G01N 21/431 356/128 |
| 2010/0071150 | A1* | 3/2010 | Kereth | B08B 1/00 15/320 |
| 2010/0315630 | A1* | 12/2010 | Ramos | G01M 3/047 356/301 |
| 2013/0057675 | A1* | 3/2013 | Jaaskelainen | G01P 5/22 348/84 |
| 2015/0219436 | A1* | 8/2015 | Obi | G01B 9/02049 356/479 |
| 2017/0122847 | A1* | 5/2017 | Canty | E21B 41/0007 |

* cited by examiner

*Primary Examiner* — Max H Noori
(74) *Attorney, Agent, or Firm* — Buchanan Ingersoll & Rooney PC

(57) ABSTRACT

An optical measuring device including a measuring head, an inner shell including a light transmitter and a light receiver, an outer shell including a measurement orifice in one end and a fastening flange part in another end, the inner shell is arranged at least partially in the outer shell, the measuring head is arranged in the outer shell and attached to the measurement orifice from its first end and to an end of the inner shell from its second end, a gasket is arranged between the measuring head and the measurement orifice, and inside the outer shell is arranged a fluid flow path extending from the gasket towards the fastening flange part, wherein to the outer shell is formed a leak detection port having one end opening into the fluid flow path and another end opening into a side surface of the outer wall in the fastening flange part wherein a fastening flange protrudes between the opening into the side surface and the measurement orifice.

16 Claims, 4 Drawing Sheets

OPTICAL MEASURING DEVICE, A REFRACTOMETER AND AN ARRANGEMENT FOR AN OPTICAL MEASUREMENT

FIELD OF THE INVENTION

The present invention relates to an optical measuring device, a refractometer and an arrangement for an optical measurement.

BACKGROUND OF THE INVENTION

Optical measuring devices are used in monitoring, controlling and managing processes. An example of an optical measuring device is a refractometer, which measures the refractive index of a process medium by means of the total reflection created at the interface between an optical window and the process medium.

The process medium measured by an optical measuring device may be hot, pressurized, aggressive or otherwise hazardous. The failure of operation, e.g. a leakage into the optical measuring device from the process, is often detected by a humidity sensor and/or the electronics inside the optical measuring device. This prevents injuries resulting from a fitting or a connection failure and protects the measuring device and the user.

If the process medium is food products, e.g. dairy, liquid food, liquid sugar or beverage, a leakage into the optical measuring device poses a contamination risk. The growth of spoilage and pathogenic bacteria starts in the leaked process medium inside the optical measuring device. Then, if the pressure on the process side drops the contaminated leaked process medium is conveyed to the process medium.

The problem with the arrangement described above is that upon a failure in the fittings or connections between the process medium and the optical measuring device the user does not notice the failure and the pressure difference between the process medium and the interior of the optical measuring device pushes the leaked process medium back to the process side. The failure may also remain undetected by a humidity sensor and/or the electronics inside the optical measuring device if they are not turned on for one reason or another.

BRIEF DESCRIPTION OF THE INVENTION

An object of the present invention is to provide an optical measuring device and an arrangement to solve the above problems. The objects of the invention are achieved by an optical measuring device and an arrangement for an optical measurement which are characterized by what is stated in the independent claims. The preferred embodiments of the invention are disclosed in the dependent claims.

The invention is based on an optical measuring device comprising a measuring head, an inner shell comprising a light transmitter and a light receiver, an outer shell comprising a measurement orifice in one end and a fastening flange part in another end, the inner shell is arranged at least partially in the outer shell, the measuring head is arranged in the outer shell and attached to the measurement orifice from its first end and to an end of the inner shell from its second end, a gasket is arranged between the measuring head and the measurement orifice, and inside the outer shell is arranged a fluid flow path extending from the gasket towards the fastening flange part, wherein to the outer shell is formed a leak detection port having one end opening into the fluid flow path and another end opening into a side surface of the outer wall in the fastening flange part wherein a fastening flange protrudes between the opening into the side surface and the measurement orifice.

The invention is based on a refractometer comprising an optical window, an inner shell comprising a light transmitter and a light receiver, an outer shell comprising a measurement orifice in one end and a fastening flange part in another end, the inner shell is arranged at least partially in the outer shell, the optical window is arranged in the outer shell and attached to the measurement orifice from its first end and to an end of the inner shell from its second end, a gasket is arranged between the optical window and the measurement orifice, and inside the outer shell is arranged a fluid flow path extending from the gasket towards the fastening flange part, wherein to the outer shell is formed a leak detection port having one end opening into the fluid flow path and another end opening into a side surface of the outer wall in the fastening flange part wherein a fastening flange protrudes between the opening into the side surface and the measurement orifice.

The invention is based on an arrangement for an optical measurement comprising an optical measuring device and a process fluid to be measured in a process space, the optical measuring device comprising a measuring head positioned in process fluid in the process space, an inner shell comprising a light transmitter and a light receiver, an outer shell comprising a measurement orifice in one end and a fastening flange part in another end, wherein the optical measuring device is fastened to the process space with the fastening flange, the inner shell is arranged at least partially in the outer shell, the measuring head is arranged in the outer shell and attached to the measurement orifice from its first end and to an end of the inner shell from its second end, a gasket is arranged between the measuring head and the measurement orifice, and inside the outer shell is arranged a fluid flow path extending from the gasket towards the fastening flange part, wherein to the outer shell is formed a leak detection port, the leak detection port having one end opening into the fluid flow path and another end opening into a side surface of the outer wall in the fastening flange part wherein a fastening flange is protruding between the opening into the side surface and the measurement orifice, and the leak detection port drains from the process space past the gasket leaked process fluid upon the gasket failure.

The optical measuring device, the refractometer and the arrangement for an optical measurement allow the user to notice a failure in the fittings or in the connections between the process medium and the optical measuring device visually. Further, the optical measuring device, the refractometer and the arrangement for an optical measurement reduce the pressure difference between the process medium and the interior of the optical measuring device containing the leaked process medium thereby reducing the risk that the leaked process medium enters back to the process side.

BRIEF DESCRIPTION OF THE FIGURES

In the following the invention will be described in greater detail by means of preferred embodiments with reference to the attached drawings, in which.

DETAILED DESCRIPTION OF THE INVENTION

Figure 1:
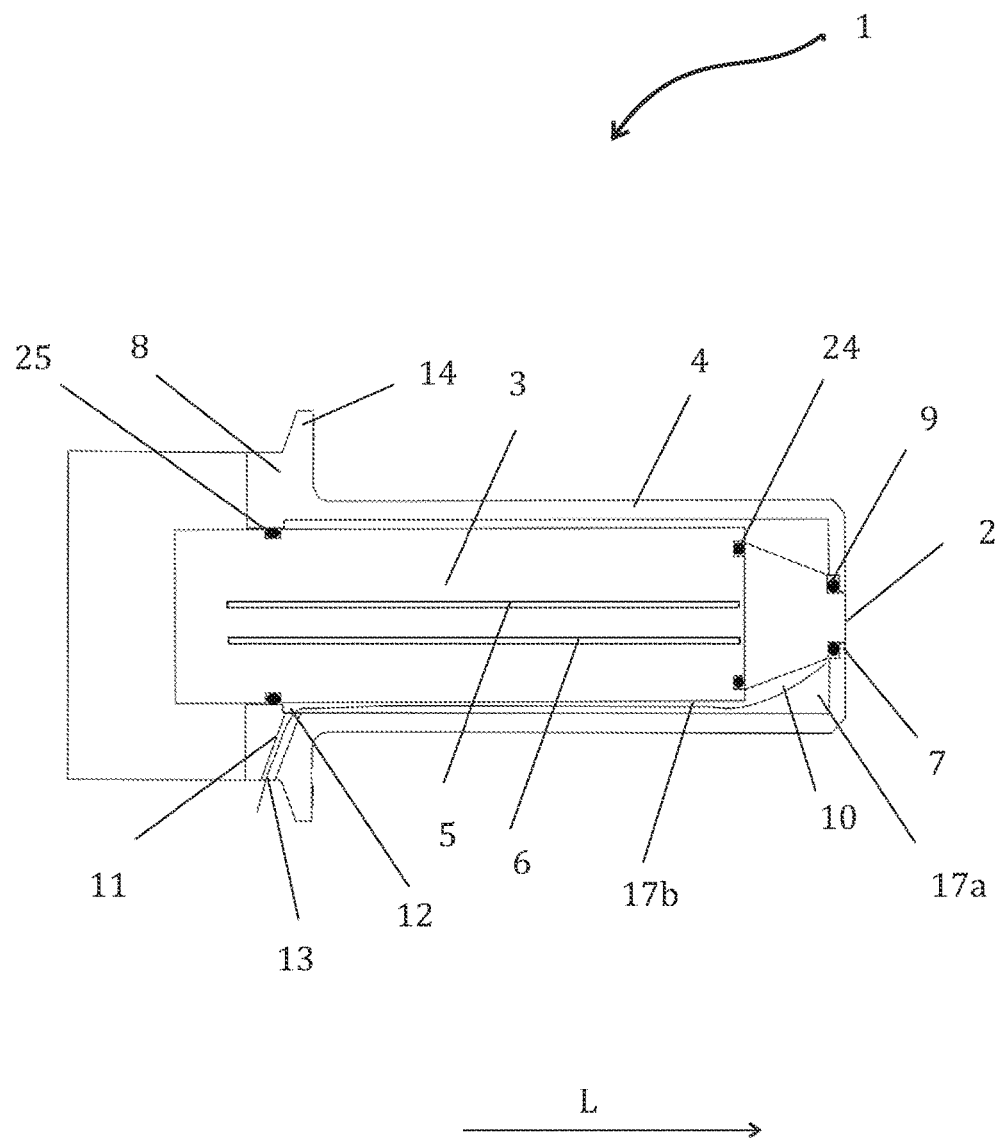
FIG. 1 shows an optical measuring device.

FIG. 1 shows an optical measuring device 1. The optical measuring device 1 comprises a measuring head 2, an inner shell 3 and an outer shell 4. The inner shell 3 comprises at least a light transmitter 5 and a light receiver 6. A light transmitter 5 and receiver 6 can comprise a fibre, for instance. The outer shell 4 comprises a measurement orifice 7 in one end and a fastening flange part 8 in another end. The measuring head 2 is arranged in the outer shell 4 and attached to the measurement orifice 7 from its first end and to an end of the inner shell 3 from its second end. The inner shell 3 is arranged at least partially in the outer shell 4 so that the outer shell 4 surrounds at least the end of inner shell 3 comprising the attachment to the measuring head 2. A gasket 9 is arranged between the measuring head 2 and the measurement orifice 7. Inside the outer shell 4 is arranged a fluid flow path 10 extending from the gasket 9 towards the fastening flange part 8. To the outer shell 4 is formed a leak detection port 11 having one end 12 opening into the fluid flow path 10 and another end 13 opening into a side surface of the outer wall in the fastening flange part 8. A fastening flange 14 protrudes between the end 12 of the leak detection port 11 opening into the side surface of the outer wall in the fastening flange part 8 and the measurement orifice 7.

Upon the gasket 9 failure, the process fluid 15 is able to flow past the gasket 9 inside the outer shell 4. The process fluid 15 is then able to flow along the fluid flow path 10 inside the outer shell 4 towards the leak detection port 11. The leak detection port 11 then drains from the process space past the gasket leaked process fluid.

The user can easily notice a failure in the gasket 9 visually as the leaked process fluid appears from the leak detection port 11. Further, as the leak detection port 11 and the fluid flow path 10 inside the outer shell 4 are open to ambient air the pressure difference between the process space 16 and the interior of the optical measuring device 1 containing the leaked process fluid is the same as between the process space 16 and the ambient air. It is advantageous that the process space 16 is in a higher pressure than the interior of the optical measuring device 1 so that the leaked process fluid flows always outwards from the process space 16. As the process fluid 15 flows typically under pressure in the process space 16, the risk that the leaked process fluid enters back to the process side is reduced.

The optical measuring device 1 may also comprise a humidity sensor and/or the electronics inside the optical measuring device capable of detecting a leakage into the optical measuring device 1 from the process space 16 in addition to the leak detection port 11. In case the failure in the gasket 9 remains undetected by a humidity sensor and/or the electronics inside the optical measuring device 1, the user is able to notice the failure in the gasket 9 visually.

In FIGS. 1-4, a fluid flow path 10 is formed by means of gaps 17a-b. There is a first gap 17a between the outer shell 4 and the measuring head 2. There is a second gap 17b between the outer shell 4 and the inner shell 3 in the length direction L of the inner 3 and outer 4 shells. The first 17a and second gaps 17b form a continuous fluid flow path 10. The second gap 17b is preferably annular.

Figure 2:
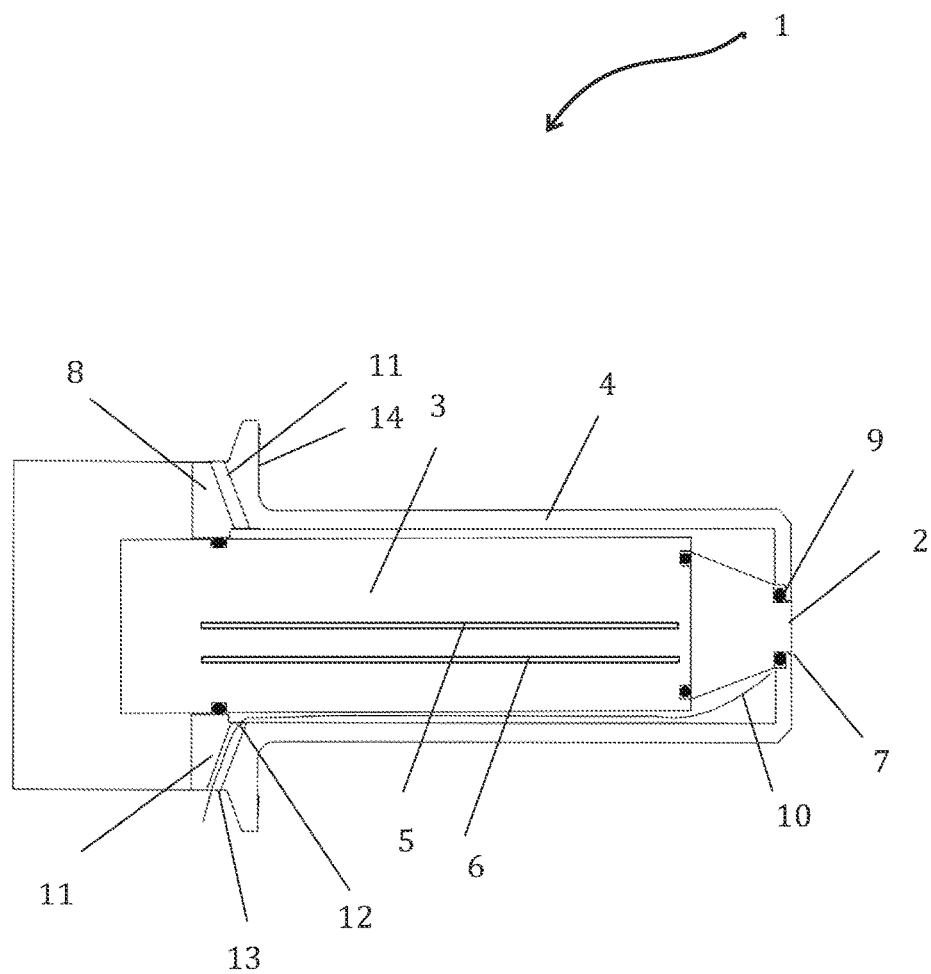
FIG. 2 shows an optical measuring device.

FIG. 2 shows an optical measuring device 2 wherein the outer shell 4 comprises two leak detection ports 11 extending through the outer shell 4. The leak detection ports 11 are positioned apart from each other in a circumferential direction of the cylindrical outer shell 4. The leak detection ports 11 can be used for rinsing the fluid flow path 10 of the from the process space leaked fluid such that the rinsing fluid enters through a first leak detection port and exits through a second leak detection port.

The outer shell 4 can comprise a plurality of leak detection ports 11 arranged to the fastening flange part 8 of the outer shell 4. The plurality of leak detection ports 11 is preferably positioned apart from each other in a circumferential direction.

An optical measuring device 1 may be an optical sensor or an optical analyser, for instance. The optical measuring device 1 is used for monitoring, controlling and managing processes, for instance.

Figure 3:
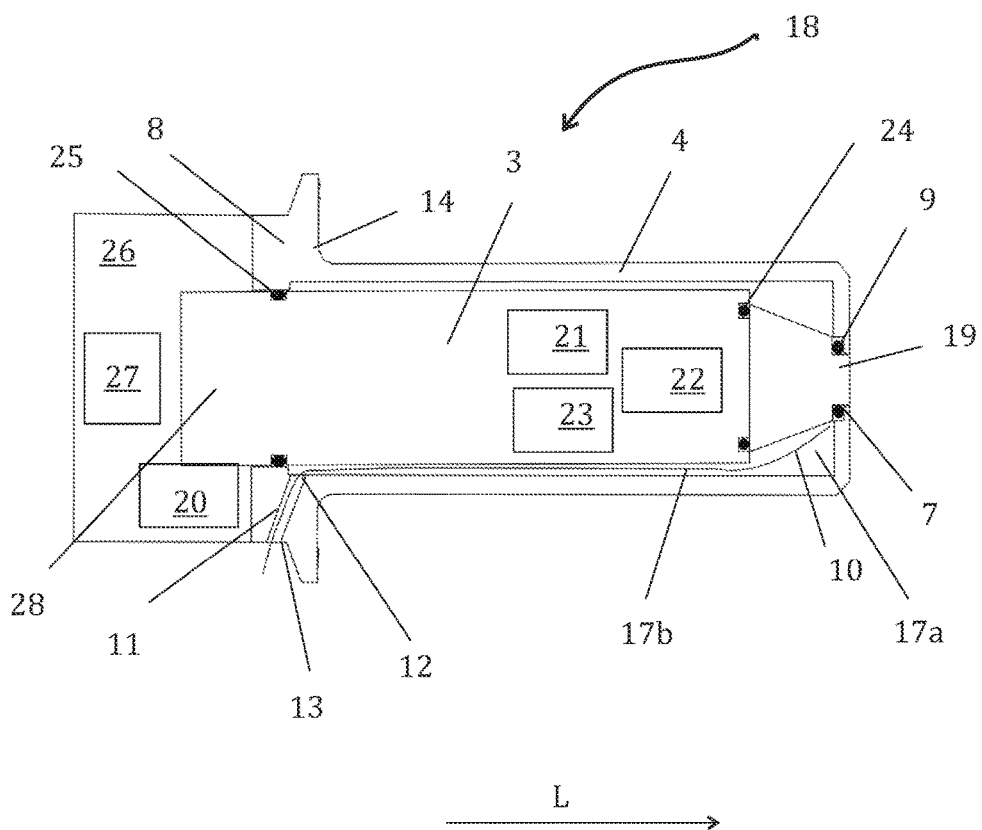
FIG. 3 shows a refractometer.

The optical measuring device of FIG. 1 or 2 comprises preferably a refractometer 18 as shown in FIG. 3. Refractometers 18 are commonly used to determine the concentration of dissolved solids by making an optical measurement of a fluid's refractive index.

As the refractometer 18 operates it measures the refractive index of a process fluid 15 by means of the total reflection created at the interface between an optical window 19 and the fluid 15. A beam of rays from a light source is directed to the interface between the optical window 19 and the process fluid 15. Part of the beam of rays is reflected from the fluid 15 entirely, part of it is absorbed partly into the fluid 15. This causes an image, in which the location of a borderline between a light area and a dark area depends on the critical angle of the total reflection and thus on the refractive index of the process fluid 15. An image detector 20 observes the image.

As shown in FIG. 3 the refractometer 18 comprises an optical window 19, an inner shell 3 and an outer shell 4. The inner shell 3 can comprise a light transmitter 5 and a light receiver 6, e.g. a transmitter fibre and a receiver fibre, as shown in FIGS. 1-2. In FIG. 3 is shown than the first shell comprises more components, a light source 21, means for directing the beam of rays 22 from the light source 21 to an interface between the optical window 19 and a fluid 15 to be measured, and a temperature detector 23. The outer shell 4 comprises a measurement orifice 7 in one end and a fastening flange part 8 in another end. The inner shell 3 is arranged at least partially in the outer shell 4 so that the outer shell 4 surrounds at least the end of inner shell 3 comprising the attachment to the optical window 19. The optical window 19 is arranged inside the outer shell 4 and attached to the measurement orifice 7 from its first end and to an end of the inner shell 3 from its second end. A gasket 9 is arranged between the optical window 19 and the measurement orifice 7. Inside the outer shell 4 is arranged a fluid flow path 10 extending from the gasket 9 towards the fastening flange part 8, wherein to the outer shell 4 is formed a leak detection port 11 having one end 12 opening into the fluid flow path 10 and another end 13 opening into a side surface of the outer wall in the fastening flange part 8. A fastening flange 8 protrudes between the end 13 of the leak detection port 11 opening into a side surface of the outer wall in the fastening flange part 8 and the measurement orifice 7.

The connections inside the outer shell 4 are preferably sealed to prevent the entering of the outdoor air and the leaked process fluid to the components inside the outer shell 4. The attachment between the optical window 19 and the end of the inner shell 3 comprises a first sealing 24. A second sealing 25 is arranged between the outer shell 4 and the inner shell 3 located such that the fluid flow path 10 terminates between the first sealing 24 and the second sealing 25.

The inner shell 3 can also comprise a sealed module. Then the second sealing between the outer shell 4 and the inner shell 3 is unnecessary, as the leaked process fluid cannot enter the inner shell 3.

The refractometer 18 can comprise a housing part 26 attached to an end part of the inner shell 28 comprising measurement electronics 27. The measurement electronics 27 may be, for example, a CCD element or camera, image analyser and the calibration electronics of the measuring device, a processing unit, an output unit or any combination of these. The housing part 26 and the end part of the inner shell 28 can be connected to each other such that the inner shell 3 opens to the housing part 26. The ambient air cannot enter the inner shell 3 or the housing part 26 due to the second sealing 25.

The measuring head 2 of a refractometer 18 comprises an optical window 19, e.g. a prism, comprising sapphire or mineral material, and preferably also a temperature detector 23.

Refractometers 18 are suitable for monitoring and optimizing the operations of food industry. For instance, they can be used in the most common operations in the dairy industry: blending, standardization, homogenization, evaporation and spray drying.

Figure 4:
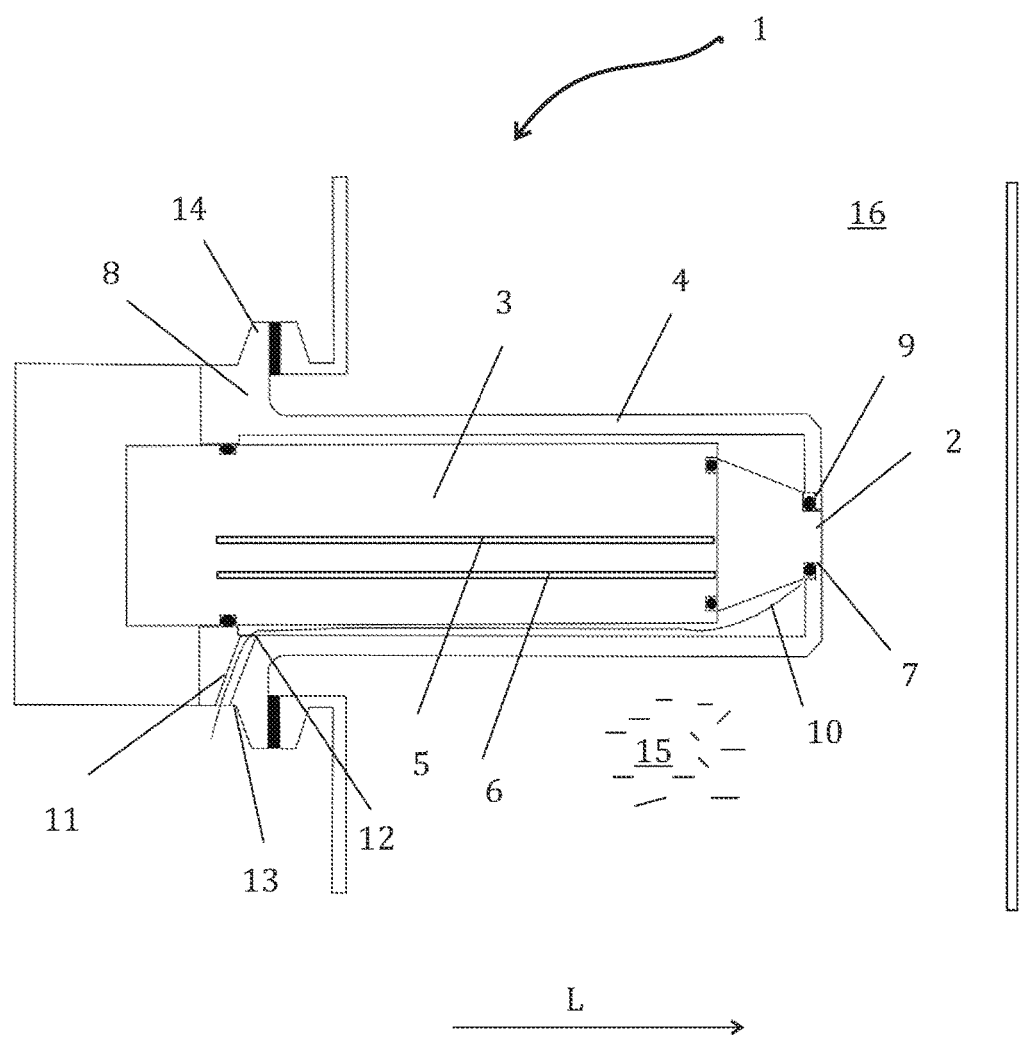
FIG. 4 shown an arrangement for an optical measurement.

FIG. 4 shows the arrangement for an optical measurement. An arrangement for an optical measurement comprises an optical measuring device 1 and a process fluid 15 in a process space 16. The process space 16 may be a process pipe, for instance. An example of the process space 16 and the process fluid 15 is a line comprising milk, milk products, dairy, liquid food or beverage.

The optical measuring device 1 comprises a measuring head 2 positioned in process fluid 15 in the process space 16. An inner shell 3 comprises at least a light transmitter 5 and a light receiver 6. An outer shell 4 comprises a measurement orifice 7 in one end and a fastening flange part 8 in another end. The optical measuring device 1 is fastened to the process space 16 with the fastening flange 14. The inner shell 3 is arranged at least partially in the outer shell 4. The measuring head 2 is arranged inside the outer shell 4. The measuring head 2 is attached to the measurement orifice 7 from its first end and to an end of the inner shell 3 from its second end. A gasket 9 is arranged between the measuring head 2 and the measurement orifice 7. Inside the outer shell 4 is arranged a fluid flow path 10 extending from the gasket 9 towards the fastening flange part 8, wherein to the outer shell 4 is formed a leak detection port 11, the leak detection port 11 having one end 12 opening into the fluid flow path 10 and another end 13 opening into a side surface of the outer wall in the fastening flange part 8. A fastening flange 14 is protruding between the end 13 opening into the side surface and the measurement orifice 7, and the leak detection port 11 drains from the process space 16 past the gasket 9 leaked process fluid 15 upon the gasket 9 failure.

As shown in FIG. 4 the outer surface of the outer shell 4 of the optical measuring device 1, is exposed to the process fluid 15 to be measured at least partially. The process fluid 15 is in contact with the outer surface of the outer shell 4 from its end comprising the measurement orifice 7 to the fastening flange 14. The outer shell 4 surrounds the inner shell 3 such that the process fluid 15 in the process space 16 cannot contact the inner shell 3. The outer shell 4 preferably comprises stainless steel or acid-proof steel, ceramics or special plastics.

The optical measuring device 1 is preferably inserted in the process space 3 with the length direction L axle of the optical measuring device 1 in a horizontal direction for a fluent draining of the leaked process fluid.

The inner shell 3 of the optical measuring device 1 extends outside the process space 16 when the measuring head 2 is in an inserted position. The inner shell 3 can also be totally contained in the outer shell 4. In the arrangement, the optical measuring device 1 is positioned in one side of the process space 16.

The gasket 9 used to seal the measuring head 2, or the optical window 19 may be a conical sealing or it may form a spherical surface or it can comprise an O ring sealing, for example.

The optical measuring device 1 shown in the arrangement in FIG. 4 can be the refractometer 18 shown in FIG. 3, for instance.

The arrangement is advantageous for in-line measurements. The optical measuring device, e.g. a refractometer, is an advantageous in-line measuring instrument for safe, clean, sanitary and accurate determination of the concentration of dissolved solids.

It will be obvious to a person skilled in the art that, as the technology advances, the inventive concept can be implemented in various ways. The invention and its embodiments are not limited to the examples described above but may vary within the scope of the claims.

List of parts: 1 an optical measuring device; 2 a measuring head; 3 an inner shell; 4 an outer shell; 5 a light transmitter; 6 a light receiver; 7 a measurement orifice; 8 a fastening flange part; 9 a gasket; 10 a fluid flow path; 11 a leak detection port; 12, 13 an end of a leak detection port; 14 a fastening flange; 15 process fluid; 16 a process space; 17 a-b a gap; 18 a refractometer; 19 an optical window; 20 an image detector; 21 a light source; 22 means for directing the beam of rays; 23 a temperature detector; 24 a first sealing; 25 a second sealing; 26 a housing part; 27 measurement electronics; 28 an end part of the inner shell; L length direction.

The invention claimed is:

1. An optical measuring device comprising:
    a measuring head;
    an inner shell having a light transmitter and a light receiver;
    an outer shell having a measurement orifice in one end and a fastening flange part in another end, the inner shell being arranged at least partially in the outer shell, the measuring head being arranged in the outer shell and attached to the measurement orifice from its first end and to an end of the inner shell from its second end;
    a gasket arranged between the measuring head and the measurement orifice; and
    inside the outer shell a fluid flow path extending from the gasket towards the fastening flange part, wherein to the outer shell is formed a leak detection port having one end opening into the fluid flow path and another end opening into a side surface of the outer wall in the fastening flange part wherein a fastening flange protrudes between the opening into the side surface and the measurement orifice.

2. An optical measuring device according to claim 1, comprising:
    a first gap between the outer shell and the measuring head and a second gap between the outer shell and the inner shell form the fluid flow path.

3. An optical measuring device according to claim 2, wherein the second gap is an annular gap.

4. An optical measuring device according to claim 1, wherein the outer shell comprises:

two leak detection ports positioned apart from each other in a circumferential direction.

5. An optical measuring device according to claim 1, wherein the inner shell comprises:
a sealed module.

6. A refractometer comprising:
an optical window;
an inner shell having a light transmitter and a light receiver;
an outer shell having a measurement orifice in one end and a fastening flange part in another end, the inner shell being arranged at least partially in the outer shell, the optical window being arranged in the outer shell and attached to the measurement orifice from its first end and to an end of the inner shell from its second end;
a gasket arranged between the optical window and the measurement orifice; and
inside the outer shell a fluid flow path extending from the gasket towards the fastening flange part, wherein to the outer shell is formed a leak detection port having one end opening into the fluid flow path and another end opening into a side surface of the outer wall in the fastening flange part wherein a fastening flange protrudes between the opening into the side surface and the measurement orifice.

7. A refractometer according to claim 6, comprising:
a first gap between the outer shell and the optical window and a second gap between the outer shell and the inner shell form the fluid flow path.

8. A refractometer according to claim 7, wherein the second gap is an annular gap.

9. A refractometer according to claim 6, wherein the outer shell comprises:
two leak detection ports positioned apart from each other in a circumferential direction.

10. A refractometer according to claim 6, wherein the attachment between the optical window and the end of the inner shell comprises:
a first sealing.

11. A refractometer according to claim 10, comprising:
between the outer shell and the inner shell, a second sealing located such that the fluid flow path terminates between the first sealing and the second sealing.

12. A refractometer according to claim 6, wherein the inner shell comprises:
a light source;
means for directing a beam of rays from the light source to an interface between the optical window and a process fluid to be measured; and
an image detector.

13. A refractometer according to claim 6, wherein the inner shell comprises:
a sealed module.

14. An arrangement for an optical measurement comprising:
an optical measuring device; and
a process space for receiving process fluid to be measured, the optical measuring device including:
a measuring head positioned in process fluid when in the process space, an inner shell having a light transmitter and a light receiver, an outer shell having a measurement orifice in one end and a fastening flange part in another end, wherein the optical measuring device is fastened to the process space with the fastening flange, the inner shell being arranged at least partially in the outer shell, the measuring head being arranged in the outer shell and attached to the measurement orifice from its first end and to an end of the inner shell from its second end, a gasket arranged between the measuring head and the measurement orifice, and inside the outer shell a fluid flow path extending from the gasket towards the fastening flange part, wherein to the outer shell is formed a leak detection port, the leak detection port having one end opening into the fluid flow path and another end opening into a side surface of the outer wall in the fastening flange part wherein a fastening flange is protruding between the opening into the side surface and the measurement orifice, and the leak detection port drains from the process space past the gasket leaked process fluid upon the gasket failure.

15. An arrangement according to claim 14, wherein the optical measuring device is inserted in the process space, with an axis of the optical measuring device in a horizontal direction.

16. An arrangement according to claim 14, wherein the optical measuring device is a refractometer.

* * * * *